US00PP14810P2

(12) United States Plant Patent
Hammons

(10) Patent No.: US PP14,810 P2
(45) Date of Patent: May 25, 2004

(54) CHRYSANTHEMUM PLANT NAMED 'SUNNY YOSHASTA'

(50) Latin Name: *Chrysanthemum×morifolium*
Varietal Denomination: Sunny Yoshasta

(75) Inventor: Donald Hammons, Travelers Rest, SC (US)

(73) Assignee: Yoder Brothers, Inc., Barberton, OH (US)

( * ) Notice: Subject to any disclaimer, the term of this patent is extended or adjusted under 35 U.S.C. 154(b) by 12 days.

(21) Appl. No.: 10/396,575

(22) Filed: Mar. 25, 2003

(51) Int. Cl.[7] ..... A01H 5/00
(52) U.S. Cl. ..... Plt./295
(58) Field of Search ..... Plt./295

*Primary Examiner*—Anne Marie Grunberg
(74) *Attorney, Agent, or Firm*—C. A. Whealy

(57) ABSTRACT

A distinct cultivar of Chrysanthemum plant named 'Sunny Yoshasta', characterized by its uniform, upright and outwardly spreading plant habit; strong and freely branching growth habit; dark green-colored foliage; uniform flowering habit; early flowering habit; numerous daisy-type inflorescences; light yellow-colored ray florets; and excellent post-production longevity with plants maintaining good substance and color for about four weeks in an interior environment.

1 Drawing Sheet

Botanical classification/cultivar designation: *Chrysanthemum×morifolium* cultivar Sunny Yoshasta.

BACKGROUND OF THE INVENTION

The present Invention relates to a new and distinct cultivar of Chrysanthemum plant, botanically known as *Chrysanthemum×morifolium* and hereinafter referred to by the name 'Sunny Yoshasta'.

The new Chrysanthemum is a naturally-occurring branch mutation of the Chrysanthemum cultivar Shasta, disclosed in U.S. Plant Pat. No. 9,314. The new Chrysanthemum was discovered and selected by the Inventor from within a population of plants of the parent cultivar in a controlled environment in Travelers Rest, S.C. in February, 1999. The selection of this branch mutation was based on its unique ray floret coloration.

Asexual reproduction of the new Chrysanthemum by vegetative tip cuttings was first conducted in Travelers Rest, S.C. Asexual reproduction by cuttings has shown that the unique features of this new Chrysanthemum are stable and reproduced true to type in successive generations.

SUMMARY OF THE INVENTION

The cultivar Sunny Yoshasta has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Sunny Yoshasta'. These characteristics in combination distinguish 'Sunny Yoshasta' as a new and distinct Chrysanthemum:

1. Uniform, upright and outwardly spreading plant habit.
2. Strong and freely branching growth habit.
3. Dark green-colored foliage.
4. Uniform flowering habit.
5. Early flowering, 8-week response time.
6. Numerous daisy-type inflorescences.

7. Light yellow-colored ray florets.
8. Excellent postproduction longevity with plants maintaining good substance and color for about four weeks in an interior environment.

Plants of the new Chrysanthemum differ primarily from plants of the cultivar Shasta in ray floret coloration as plants of the new Chrysanthemum have light yellow-colored ray florets whereas plants of the cultivar Shasta have white-colored ray florets. In addition, plants of the new Chrysanthemum flower about one to three days later than plants of the parent.

Plants of the new Chrysanthemum can be compared to plants of the cultivar Yochesapeake, disclosed in U.S. Plant Pat. No. 12,535. In side-by-side comparisons conducted in Salinas, Calif., plants of the new Chrysanthemum differed from plants of the cultivar Yochesapeake in the following characteristics:

1. Plants of the new Chrysanthemum were shorter and more outwardly spreading than plants of the cultivar Yochesapeake.
2. Plants of the new Chrysanthemum had light yellow-colored ray florets whereas plants of the cultivar Yochesapeake had darker yellow-colored ray florets.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the sheet comprises a side perspective view of typical flowering plants of 'Sunny Yoshasta' grown as spray-types.

The photograph at the bottom of the sheet comprises a close-up view of typical inflorescences of 'Sunny Yoshasta' grown as spray-types.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the fall in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At the time of the pinch, the photoinductive short day/long night treatments were initiated. Plants used for the photographs and description were grown as spray-types. Measurements and numerical values represent averages of typical flowering plants.

Botanical classification: *Chrysanthemum×morifolium* cultivar Sunny Yoshasta.

Commercial classification: Daisy-type potted Chrysanthemum.

Parentage: Naturally-occurring branch mutation of *Chrysanthemum×morifolium* cultivar Shasta, disclosed in U.S. Plant Pat. No. 9,314.

Propagation:

*Type.*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching.

Plant description:

*Appearance.*—Herbaceous daisy-type potted Chrysanthemum that is typically grown as a spray-type. Uniform with lateral branches upright and outwardly spreading; uniformly mounded crown. Strong and freely branching growth habit; about five lateral branches develop after removal of terminal apex (pinching); dense and full plants.

*Plant height.*—About 26 cm.

*Plant width.*—About 47 cm.

*Lateral branches.*—Length: About 21 cm. Diameter: About 5 mm. Internode length: About 1.25 cm. Strength: Strong. Texture: Pubescent. Color: Close to 146A.

*Foliage description.*—Arrangement: Alternate; simple. Length: About 6.9 cm. Width: About 4.8 cm. Apex: Cuspidate. Base: Truncate. Margin: Palmately lobed, sinuses between lateral lobes mostly parallel to convergent. Texture, upper surface: Sparsely pubescent. Texture, lower surface: Pubescent; veins prominent. Color: Developing and fully expanded foliage, upper surface: 147A. Developing and fully expanded foliage, lower surface: 147B. Venation, upper and lower surfaces: 147B. Petiole length: About 1.75 cm. Petiole diameter: About 3 mm. Petiole color, upper and lower surfaces: 147B to 147C.

Inflorescence description:

*Appearance.*—Daisy-type inflorescence form with elongated oblong-shaped ray florets. Inflorescences borne on terminals above foliage. Disk and ray florets develop acropetally on a capitulum. Inflorescences not fragrant. Plants are typically grown as spray-types.

*Flowering response*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to three weeks of long day/short night conditions followed by photoinductive short day/long night conditions flower about eight weeks later.

*Postproduction longevity.*—Inflorescences maintain good color and substance for about four weeks in an interior environment.

*Quantity of inflorescences.*—Freely flowering, about seven inflorescences develop per lateral branch.

*Inflorescence bud.*—Height: About 5 mm. Diameter: About 7 mm. Shape: Oblate. Color: Between 146A and 147A.

*Inflorescence diameter.*—About 6.75 cm.

*Inflorescence depth (height).*—About 2.3 cm.

*Diameter of disc.*—About 1.7 cm.

*Receptacle diameter.*—About 7 mm.

*Ray florets.*—Shape: Elongated oblong. Orientation: Initially upright, then about 65° from vertical. Aspect: Mostly straight and flat. Length: About 3.4 cm. Corolla tube length: About 3.5 mm. Width: About 1.3 cm. Apex: Emarginate. Base: Fused into a corolla tube. Margin: Entire. Texture: Smooth, glabrous, satiny. Number of ray florets per inflorescence: About 30 arranged in two or three whorls. Color: When opening, upper surface: Close to 4A. When opening, lower surface: Close to 4D. Fully opened, upper surface: Close to 4A to 4B. Fully opened, lower surface: Close to 4D to lighter than 4D.

*Disc florets.*—Arrangement: Massed at center of receptacle. Shape: Tubular, elongated. Apex: Five-pointed. Length: About 6.5 mm. Diameter, apex: About 1.25 mm. Diameter, base: About 1 mm. Number of disc florets per inflorescence: About 178. Color: Immature: Close to 154A. Mature: Apex: 6A. Mid-section: 154D. Base: Close to 155D.

*Peduncles.*—Length: First peduncle: About 4.8 cm. Fourth peduncle: About 9.5 cm. Seventh peduncle: About 10.8 cm. Diameter: About 3 mm. Angle to vertical: About 45° from vertical. Strength: Strong, flexible. Texture: Pubescent. Color: 146A.

*Phyllaries.*—Quantity per inflorescence: About 24. Length: About 7 mm. Width: About 2 mm. Shape: Deltoid. Apex: Acute. Base: Truncate. Margin: Entire. Texture, upper surface: Waxy, smooth. Texture, lower surface: Pubescent. Color, upper surface: Close to 146A. Color, lower surface: 146A to 147A.

*Reproductive organs.*—Androecium: Present on disc florets only. Anther color: Close to 9A. Pollen amount: None observed. Gynoecium: Present on both ray and disc florets. Style color: Close to 144B to 144C. Stigma color: Close to 9A.

*Seed/fruit.*—Seed and fruit production has not been observed.

Disease/pest resistance: Resistance to pathogens and pests common to Chrysanthemums has not been observed on plants grown under commercial greenhouse conditions.

It is claimed:

1. A new and distinct cultivar of Chrysanthemum plant named 'Sunny Yoshasta', as illustrated and described.

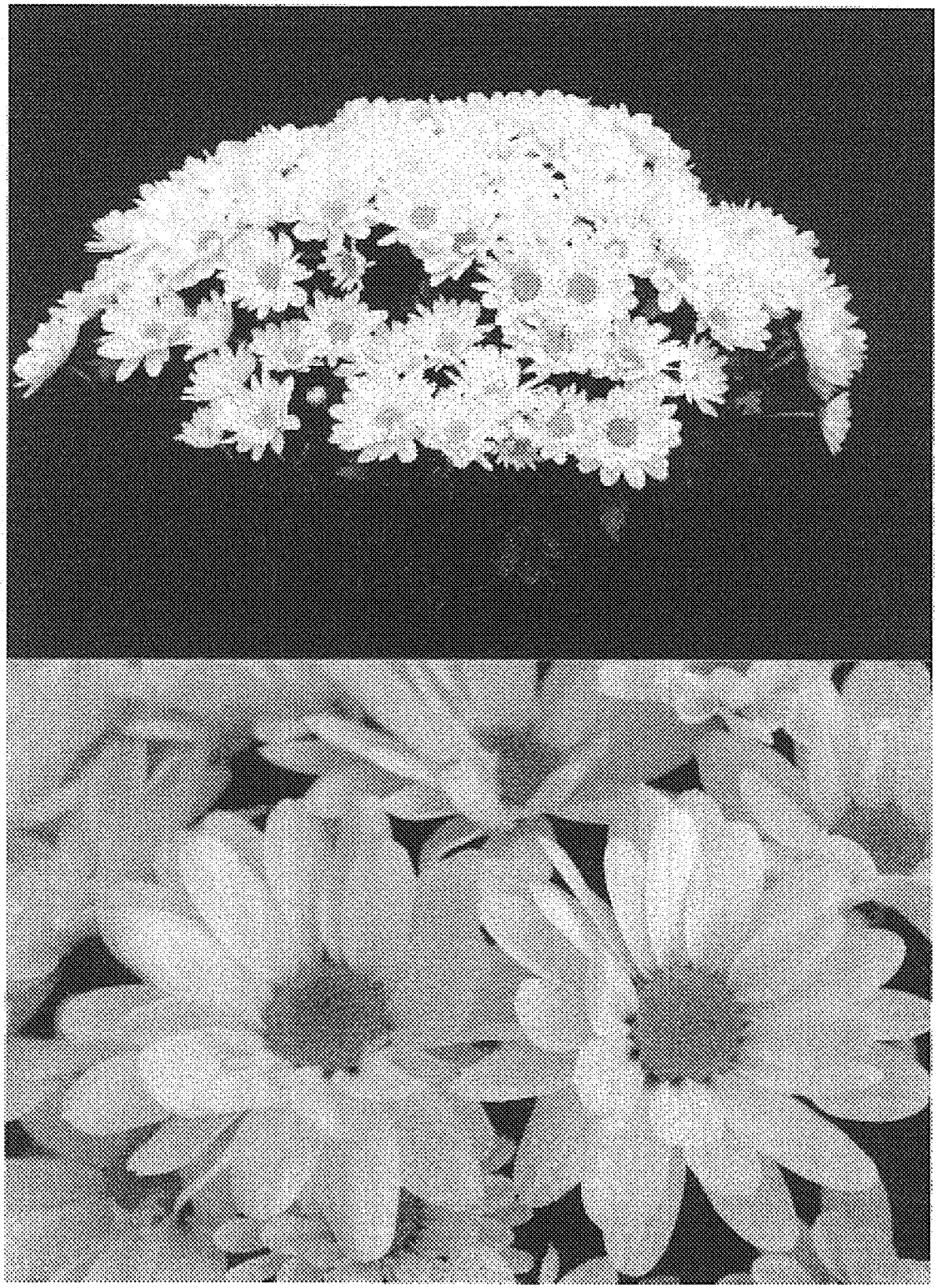

* * * * *